(12) United States Patent
Komatsubara

(10) Patent No.: US 10,849,313 B2
(45) Date of Patent: Dec. 1, 2020

(54) ABSORBENT ARTICLE FOR ANIMALS

(71) Applicant: UNICHARM CORPORATION, Ehime (JP)

(72) Inventor: Daisuke Komatsubara, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 258 days.

(21) Appl. No.: 16/066,301

(22) PCT Filed: Sep. 14, 2016

(86) PCT No.: PCT/JP2016/077173
§ 371 (c)(1),
(2) Date: Jun. 27, 2018

(87) PCT Pub. No.: WO2017/115501
PCT Pub. Date: Jul. 6, 2017

(65) Prior Publication Data
US 2019/0014747 A1 Jan. 17, 2019

(30) Foreign Application Priority Data
Dec. 28, 2015 (JP) ................... 2015-257385

(51) Int. Cl.
*A01K 23/00* (2006.01)
*A61F 13/494* (2006.01)
(Continued)

(52) U.S. Cl.
CPC ............ *A01K 23/00* (2013.01); *A61F 13/494* (2013.01); *A61F 13/622* (2013.01); *A61F 2013/15186* (2013.01)

(58) Field of Classification Search
CPC ...... A01K 23/00; A01K 29/00; B32B 37/144; A61F 13/15593; A61F 13/49015;
(Continued)

(56) References Cited

U.S. PATENT DOCUMENTS 4,537,153 A * 8/1985 Vidal ............... A01K 23/00
119/868
5,005,525 A * 4/1991 Stanton .............. A01K 23/00
119/838
(Continued)

FOREIGN PATENT DOCUMENTS

EP 2932835 A1 10/2015
JP 2003-47360 A 2/2003
(Continued)

OTHER PUBLICATIONS

International Search Report in PCT/JP2016/077173, dated Oct. 18, 2016, 4pp.

*Primary Examiner* — Richard T Price, Jr.
(74) *Attorney, Agent, or Firm* — Hauptman Ham, LLP

(57) ABSTRACT

An absorbent article for animals includes: a support body part which is detachably worn around the waist including the back and belly of the animal; and an absorbent main body part which is disposed along the back, crotch and belly of the animal and is detachably engaged with and fixed to the support body part. When viewed in a planar view in an unfolded state, the absorbent main body part is provided with: an engagement part which is disposed on at least one of end parts which are located at both longitudinal ends; an absorbent body; a tail opening part; and elastic members which impart a longitudinal contractive force to the absorbent main body part. The elastic members are disposed on both widthwise outer sides of the absorbent body and have a longer longitudinal length than the longitudinal length of the absorbent body.

7 Claims, 5 Drawing Sheets

(51) Int. Cl.
*A61F 13/62* (2006.01)
*A61F 13/15* (2006.01)

(58) Field of Classification Search
CPC .......... A61F 13/496; A61F 2013/15146; A61F 2013/15186; B65H 39/16
USPC .................. 119/850, 792, 867–869, 856
See application file for complete search history.

(56) References Cited

U.S. PATENT DOCUMENTS

| | | | | |
|---|---|---|---|---|
| 5,463,985 A * | 11/1995 | Shover | ................ | A01K 13/006 119/850 |
| 5,555,847 A * | 9/1996 | Kelly | ................ | A01K 23/00 119/850 |
| 6,070,557 A * | 6/2000 | Hibbert | ................ | A01K 13/006 119/850 |
| 6,142,105 A * | 11/2000 | McKnight | ................ | A01K 23/00 119/850 |
| 6,368,313 B1 * | 4/2002 | Howard | ................ | A01K 23/00 119/850 |
| 6,557,497 B1 * | 5/2003 | Milligan | ................ | A01K 23/00 119/850 |
| D480,842 S * | 10/2003 | Grodecki | ................ | 119/869 |
| 6,675,745 B1 * | 1/2004 | Brewington | ................ | A01K 23/00 119/850 |
| 7,464,668 B2 * | 12/2008 | Brewington | ................ | A01K 23/00 119/850 |
| 7,753,008 B2 * | 7/2010 | Krenkel | ................ | A01K 23/00 119/868 |
| 7,975,656 B2 * | 7/2011 | Prill | ................ | A01K 13/006 119/850 |
| 8,807,090 B1 * | 8/2014 | Potts | ................ | A01K 23/00 119/850 |
| 8,893,663 B2 * | 11/2014 | Curtis | ................ | A61D 9/00 119/725 |
| 8,992,495 B1 * | 3/2015 | Howell | ................ | A01K 23/00 119/868 |
| 2007/0163520 A1 * | 7/2007 | Krenkel | ................ | A01K 23/00 119/869 |
| 2014/0076245 A1 | 3/2014 | Komatsubara et al. | | |
| 2018/0016178 A1 * | 1/2018 | Cho | ................ | C03B 23/0302 |
| 2019/0014747 A1 * | 1/2019 | Komatsubara | ........ | A01K 23/00 |
| 2019/0083326 A1 * | 3/2019 | Komatsubara | .... | A61F 13/49011 |
| 2019/0191668 A1 * | 6/2019 | Yamamoto | ............ | A01K 23/00 |
| 2019/0327937 A1 * | 10/2019 | Yamamoto | ............ | A01K 23/00 |

FOREIGN PATENT DOCUMENTS

| | | |
|---|---|---|
| JP | 2006-122039 A | 5/2006 |
| JP | 2012-139128 A | 7/2012 |
| JP | 2013-46587 A | 3/2013 |
| JP | 2014-226111 A | 12/2014 |
| WO | 2012/132891 A1 | 10/2012 |

* cited by examiner

ABSORBENT ARTICLE FOR ANIMALS

RELATED APPLICATIONS

The present application is a National Phase of International Application Number PCT/JP2016/077173, filed Sep. 14, 2016, and claims priority to Japanese Application No. 2015-257385, filed Dec. 28, 2015.

FIELD

The present invention relates to an absorbent article for an animal, such as a disposable diaper, to be used for an animal such as a dog or cat.

BACKGROUND

Known absorbent articles for animals, for treatment of excreta that have been excreted by a pet such as a dog, include absorbent body-comprising belt-shaped disposable diapers that are worn by being wrapped around the torso of the pet.

As an example of such an absorbent article for an animal, PTL 1 proposes a two-part paper diaper for a bedridden pet, comprising a belt of a stretchable material that is initially wrapped around the torso of a pet, and a diaper body provided with an absorbent body having a structure that is raised into angles at both flanks, wherein the stretchable material used has perforations formed at the front part of the diaper body, and is divided into slits at the rear part of the diaper body. The paper diaper for a pet disclosed in PTL 1, which uses a stretchable material that is dividable and divided at the front part and rear part of the diaper body, can fit alterations in the right-left balance of the body shape when the pet lies on its side, and can prevent side leakage of urine or feces by the absorbent body having the structure with angles at both flanks.

CITATION LIST

Patent Literature

[PTL 1] Japanese Unexamined Patent Publication No. 2006-122039

SUMMARY

Technical Problem

However, in the paper diaper disclosed in PTL 1, the diaper body and the belt of the stretchable material to be wrapped around the torso of the pet are joined together by adhesive tape provided on the outer side of the belt and the inner side of the diaper body, and therefore when the pet moves after the paper diaper has been fitted onto the pet, force in the girth direction of the pet and force in the direction crossing the girth direction (i.e., the front-back direction of the pet) act as shear forces at the joining section between the belt and the diaper body, due to stretching in the girth direction by the stretchable material of the belt and stretching in the front-back direction of the pet by the stretchable material of the diaper body, and as a result, the joined state at the joining section can no longer be maintained and the diaper body has often become disconnected from the belt.

Moreover, when both flanks of the absorbent body are merely formed at angles, then a gap tends to form between the body surface of the pet and the diaper body at the lower crotch region when the pet has moved, since this is an area around the legs that experiences a large degree of movement, and the diaper body sections (especially the edges in the widthwise direction) have been less able to deform in a manner following movement of the lower crotch region, such that leakage of excreta such as urine has often occurred through the gap formed between the body surface of the pet and the diaper body.

It is therefore an object of the present invention to provide an absorbent article for an animal that can prevent leakage of excreta, by being unlikely to detach from the body of an animal and by exactly fitting to the lower crotch region of the animal.

Solution to Problem

One aspect (aspect 1) of the invention is an absorbent article for an animal comprising a support section that is fitted in a freely detachable manner along the region around the torso including the dorsal region and abdominal region of the animal and has a torso-facing surface facing the region around the torso of the animal and a non-torso-facing surface located on the side opposite the torso-facing surface, and an absorbing body section disposed along the dorsal region, lower crotch region and abdominal region of the animal and having at least one end section, from among the dorsal region side end section located on the dorsal region side of the animal and the abdominal region side end section located on the abdominal region side of the animal, engaged and fastened in a freely detachable manner with the non-torso-facing surface of the support section, wherein the absorbing body section has a longitudinal shape with a lengthwise direction and a widthwise direction in the planar view when in the expanded state, while having a first surface as the surface facing the animal when the absorbent article for an animal is fitted onto the animal, and a second surface as the surface on the opposite side from the first surface, and the absorbing body section comprises, in the planar view when in the expanded state, an engagement section disposed on the first surface of at least one end section, from among the dorsal region side end section and the abdominal region side end section located at both ends in the lengthwise direction of the absorbing body section, an absorbent body disposed so that it extends in the lengthwise direction in a manner straddling a center axis line running in the widthwise direction of the absorbing body section and so that it extends in the widthwise direction straddling a center axis line running in the lengthwise direction, a tail opening formed between the absorbent body and the dorsal region side end section, and elastic members that impart contractive force to the absorbing body section in the lengthwise direction, the elastic members being disposed on both outer sides in the widthwise direction of the absorbent body and having lengths in the lengthwise direction that are at least longer than the length of the absorbent body in the lengthwise direction.

Since the absorbent article for an animal according to aspect 1 has an absorbing body section that comprises the engagement section disposed on the first surface of at least one end section, from among the dorsal region side end section and the abdominal region side end section located at both ends in the lengthwise direction of the absorbing body section, a tail opening formed between the absorbent body and the dorsal region side end section, and elastic members that are disposed on both outer sides in the widthwise direction of the absorbent body and have lengths in the lengthwise direction that are at least longer than the length of the absorbent body in the lengthwise direction, and that impart contractive force to the absorbing body section in the lengthwise direction, when the tail of the animal has been inserted through the tail opening to fit the absorbent article for an animal onto the body of the animal, contractive force of the elastic members acting between the dorsal region side end section and tail opening and between the abdominal region side end section and tail opening of the absorbing body section causes the engagement section of the absorbing body section to be pulled along the body surface of the animal and toward the tail opening that has a fixed location due to the tail of the animal, such that force in the direction crossing with the girth direction of the animal (shearing force) acts on the section where the engagement section of the absorbing body section and the non-torso-facing surface of the support section are engaged, thus strengthening engagement between the engagement section of the absorbing body section and the non-torso-facing surface of the support section and rendering the absorbing body section less likely to detach from the support section.

Furthermore, when the absorbent article for an animal of aspect 1 is fitted onto the body of an animal, the section of the absorbing body section facing the lower crotch region of the animal (hereunder also referred to as "lower crotch region-facing section") is relatively pulled toward both the abdominal region side end section and the tail opening by contractive force of the elastic members acting between the abdominal region side end section and tail opening of the absorbing body section, and therefore the lower crotch region-facing section more easily contacts with the lower crotch region of the animal (i.e., a gap is less likely to form between the body surface of the animal and the surface of the absorbing body section). Moreover, in the absorbing body section, since the regions on both outer sides in the widthwise direction of the absorbent body are the regions corresponding to the leg-surrounding regions of the animal, placement of the elastic members in these regions facilitates elastic deformation of the regions to follow movement of the leg-surrounding regions of the animal, and allows the regions to be fitted more exactly and persistently to the lower crotch region of the animal even during movement by the animal, such as walking.

Therefore, the absorbent article for an animal of aspect 1 can prevent leakage of excreta by the animal, by being unlikely to detach from the body of the animal and by exactly fitting to the lower crotch region of the animal.

According to another aspect (aspect 2) of the invention, in the absorbent article for an animal of aspect 1, the engagement section of the absorbing body section has at least partially a non-stretchable portion.

Since the engagement section of the absorbing body section in the absorbent article for an animal of aspect 2 has at least partially a non-stretchable portion, the structure of each engagement section is less likely to change, and engagement between the engagement section and the non-torso-facing surface of the support section is even less likely to detach.

According to another aspect (aspect 3) of the invention, the support section of the absorbent article for an animal of aspect 1 or 2 is stretchable in the girth direction of the animal.

Since the support section in the absorbent article for an animal of aspect 3 is stretchable in the girth direction of the animal, force in the direction crossing with the girth direction of the animal (shearing force), especially when the animal has moved, acts more powerfully at the portion where the engagement section of the absorbing body section and the non-torso-facing surface of the support section have engaged, thus producing more firm engagement between the engagement section of the absorbing body section and the non-torso-facing surface of the support section. This makes the absorbing body section even less likely to detach from the support section.

In addition, since the support section can be more exactly fitted to the region around the torso of the animal if the support section is stretchable in the girth direction of the animal, it is thus possible to prevent dislocation or slipping off of the support section, and therefore the absorbent article for an animal, from the body of the animal.

The absorbent article for an animal of aspect 3 can thus more stably prevent leakage of excreta of the animal.

Another aspect (aspect 4) of the invention is the absorbent article for an animal according to any one of aspects 1 to 3 wherein the support section is constructed by a single sheet-like member that has a first direction corresponding to the girth direction of the animal and a second direction that is orthogonal to the first direction, while also having a torso-facing surface facing the region around the torso of the animal and a non-torso-facing surface located on the side opposite the torso-facing surface, the sheet-like member having a support section engagement section that is able to engage with the non-torso-facing surface of the support section, on the torso-facing surface of one of the end sections among both end sections in the first direction.

In the absorbent article for an animal of aspect 4, since the sheet-like member composing the support section has a support section engagement section that is able to engage with the non-torso-facing surface of the support section, on the torso-facing surface at one of the end sections among both end sections in the first direction that corresponds to the girth direction of the animal, it is possible to match the support section to the size of the torso of the animal for exact fitting, and to effectively prevent dislocation or slipping off of the support section, and therefore the absorbent article for an animal, from the body of the animal. This allows the absorbent article for an animal of aspect 4 to more stably prevent leakage of excreta of the animal.

According to another aspect (aspect 5) of the invention, in the absorbent article for an animal of any one of aspects 1 to 4, the absorbing body section has a thickness direction that is orthogonal to both the lengthwise direction and the widthwise direction, while being composed of a laminated body that includes, in the thickness direction, at least a liquid-permeable top sheet located on the first surface side, a liquid-impermeable back sheet located on the second surface side, the absorbent body disposed between both of these sheets, and a pair of side sheets located on the first surface side of the top sheet, wherein the laminated body has a border section with a different number of layers in the widthwise direction, in the planar view with the absorbing body section in the expanded state, and the engagement section of the absorbing body section is disposed so that it extends in the widthwise direction straddling at least the border section.

Since the border section with a different number of layers for the laminated body composing the absorbing body section is the section at a point where the rigidity changes, deformation or tearing of the absorbing body section tends to occur from the border section as an origin, but if the engagement section is disposed straddling such border section, then when the engagement section has been engaged and fastened with the non-torso-facing surface of the support section, the section that tends to undergo deformation or tearing will also be engaged and fastened at the support section, and therefore deformation or tearing of the absorbing body section from the border section as an origin will be less likely to occur. This allows the absorbent article for an animal of aspect 5 to more stably and reliably prevent leakage of excreta of the animal.

According to another aspect (aspect 6) of the invention, in the absorbent article for an animal according to any one of aspects 1 to 5, on the first surface on at least one end section among the dorsal region side end section and abdominal region side end section located at both ends in the lengthwise direction of the absorbing body section, the engagement section of the absorbing body section is disposed in the region that includes an edge in the lengthwise direction of the absorbing body section.

Since the absorbent article for an animal of aspect 6 has the engagement section of the absorbing body section disposed in the region that includes the edge in the lengthwise direction of the absorbing body section, on the first surface on at least one end section among the dorsal region side end section and abdominal region side end section located at both ends in the lengthwise direction of the absorbing body section, when the engagement section of the absorbing body section is engaged and fastened with the non-torso-facing surface of the support section, it can be engaged and fastened up to the edge in the lengthwise direction of the absorbing body section, and this makes it less likely that the edge will crimp in the lengthwise direction of the absorbing body section or that the edge will catch onto the claws of the animal or onto external structures, causing the engagement between the engagement section of the absorbing body section and the non-torso-facing surface of the support section to become detached.

Thus, the absorbent article for an animal of aspect 6 allows the absorbing body section to be fitted onto the animal in a more steady manner, and as a result, leakage of excreta of the animal can be more stably and reliably prevented.

According to another aspect (aspect 7) of the invention, in an absorbent article for an animal according to any one of aspects 1 to 6, the engagement section of the absorbing body section has a plurality of engaging protrusions that protrude from the first surface, each of the plurality of engaging protrusions having a shaft portion running from the first surface of the absorbing body section and, at the tip of the shaft portion, a wide portion running in the direction in which the outer peripheral surface of the shaft portion widens.

Since each of the plurality of engaging protrusions in the engagement section of the absorbing body section of the absorbent article for an animal of aspect 7 has a shaft portion running from the first surface of the absorbing body section and, at the tip of the shaft portion, a wide portion running in the direction in which the outer peripheral surface of the shaft portion widens, when the engagement section of the absorbing body section has been engaged and fastened with the non-torso-facing surface of the support section, even if the engagement section of the absorbing body section has been pulled in different directions by movement of the animal, the engagement section can respond to forces in different directions on the non-torso-facing surface of the support section, making it able to engage with the non-torso-facing surface of the support section, so that the engagement between the engagement section of the absorbing body section and the non-torso-facing surface of the support section can be maintained in a firm state. This makes the absorbing body section even less likely to detach from the support section.

Moreover, if the engagement section of the absorbing body section is composed of the aforementioned specific engaging protrusions, the engaging protrusions can engage with any desired fiber structure such as a nonwoven fabric, thus eliminating the need to provide a loop structure that is engageable with the engaging protrusions, on the non-torso-facing surface of the support section where the engagement section engages, and the absorbing body section can be constructed with any arbitrary adjustable location where it may be engaged and fastened with the support section. Thus, the absorbent article for an animal of aspect 7 can be fitted so that the lower crotch region-facing section of the absorbing body section exactly fits the lower crotch region of the animal.

This allows the absorbent article for an animal of aspect 7 to more stably and reliably prevent leakage of excreta of the animal.

Advantageous Effects of Invention

According to the invention it is possible to provide an absorbent article for an animal that can prevent leakage of excreta, by being unlikely to detach from the body of an animal and by exactly fitting to the lower crotch region of the animal.

DESCRIPTION OF EMBODIMENTS

The disposable diaper 1 for a pet, as a preferred embodiment of the absorbent article for an animal of the invention, will now be explained in greater detail with reference to the accompanying drawings. Throughout the present description, unless otherwise specified, the concept of "viewing an object (for example, an absorbent article, support section or absorbing body section) on the horizontal plane in the expanded state in the thickness direction of the object, from the upper side in the vertical direction (the top sheet side, when the object is an absorbing body section)", will be referred to simply by the phrase "in the planar view".

The directions used throughout the present description are as follows, unless otherwise specified.

Throughout the present description, the "widthwise direction DW" is the "short direction of the lengths of a longitudinal object (for example, an absorbing body section or absorbent body) in the planar view (short direction)", the "lengthwise direction DL" is the "long direction of the lengths of a longitudinal object in the planar view", the "thickness direction DT" is the "vertical direction with respect to an object placed on the horizontal plane in the expanded state", and the widthwise direction DW, lengthwise direction DL and thickness direction DT are in a mutually orthogonal relationship.

Also, throughout the present description, the concept of the "relatively proximal side in the widthwise direction DW of a longitudinal object (for example, an absorbing body section or absorbent body), with respect to a center axis line $C_L$ running in the lengthwise direction DL" will be referred to as the "inner side in the widthwise direction", and the concept of the "relatively distal side in the widthwise direction DW of a longitudinal object, with respect to a center axis line $C_L$ running in the lengthwise direction DL" will be referred to as the "outer side in the widthwise direction". Similarly, the concept of the "relatively proximal side in the lengthwise direction DL of a longitudinal object with respect to a center axis line $C_W$ running in the widthwise direction DW" will be referred to as the "inner side in the lengthwise direction", and the concept of the "relatively distal side in the lengthwise direction DL of a longitudinal object, with respect to a center axis line $C_W$ running in the widthwise direction DW" will be referred to as the "outer side in the lengthwise direction".

Figure 1:
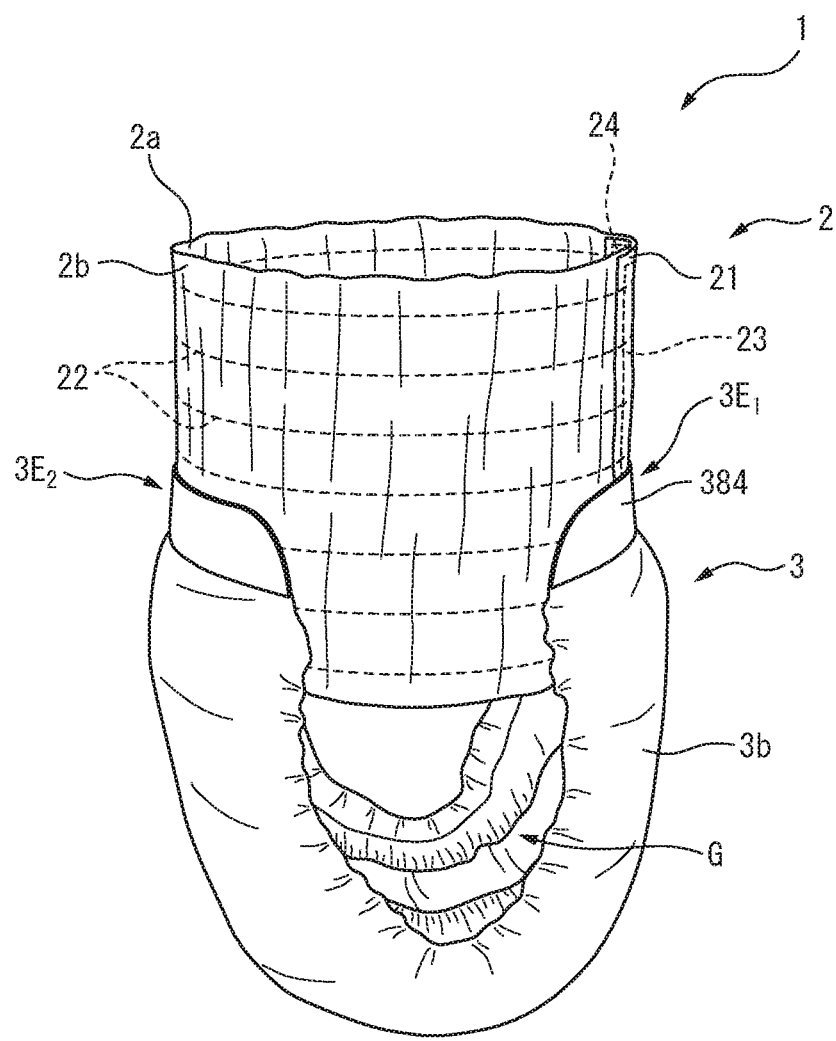
FIG. 1 is a perspective view of a disposable diaper 1 for a pet, according to an embodiment of the invention.
Figure 2:
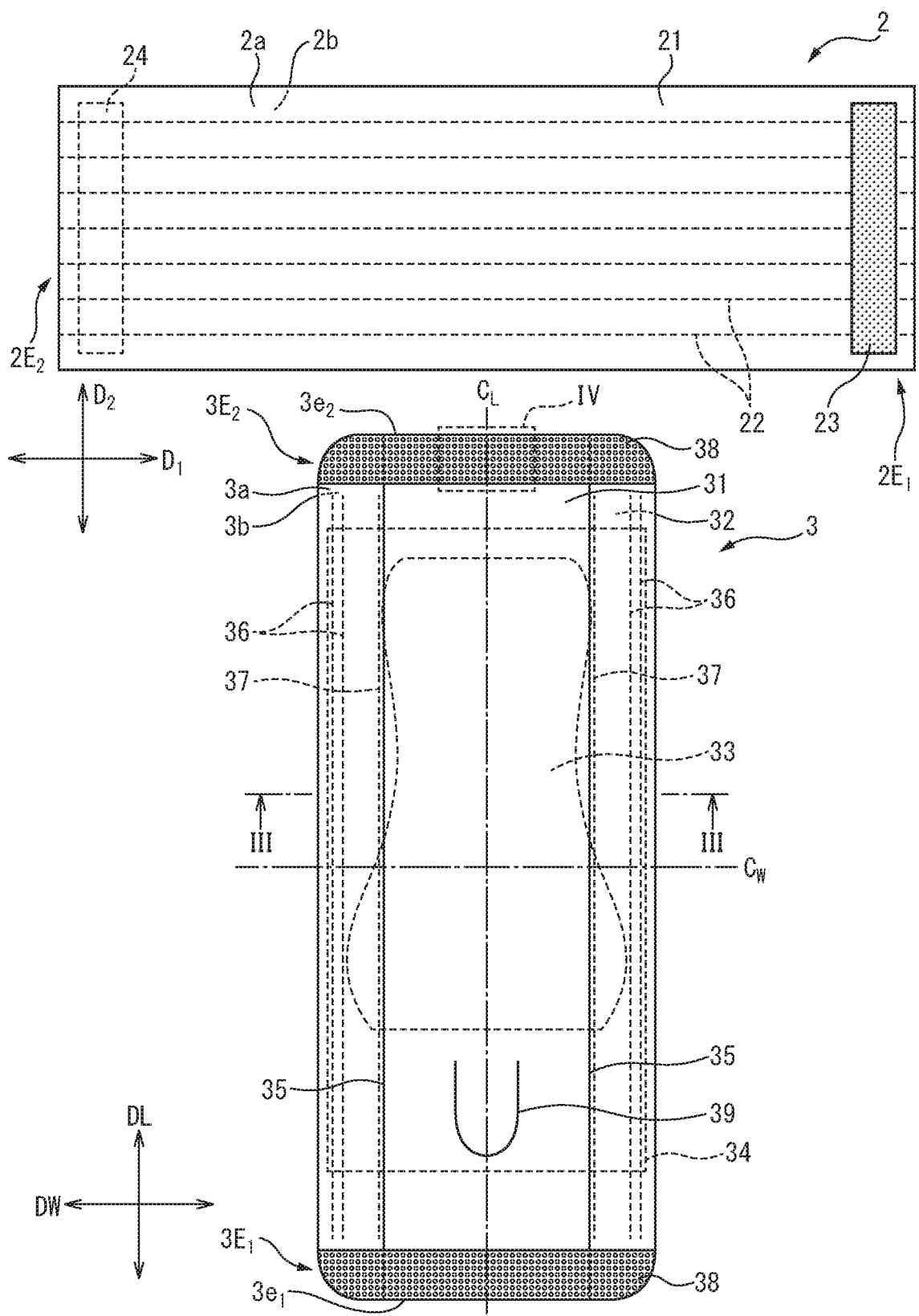
FIG. 2 is a plan view of the disposable diaper 1 for a pet, in the expanded state.
Figure 3:
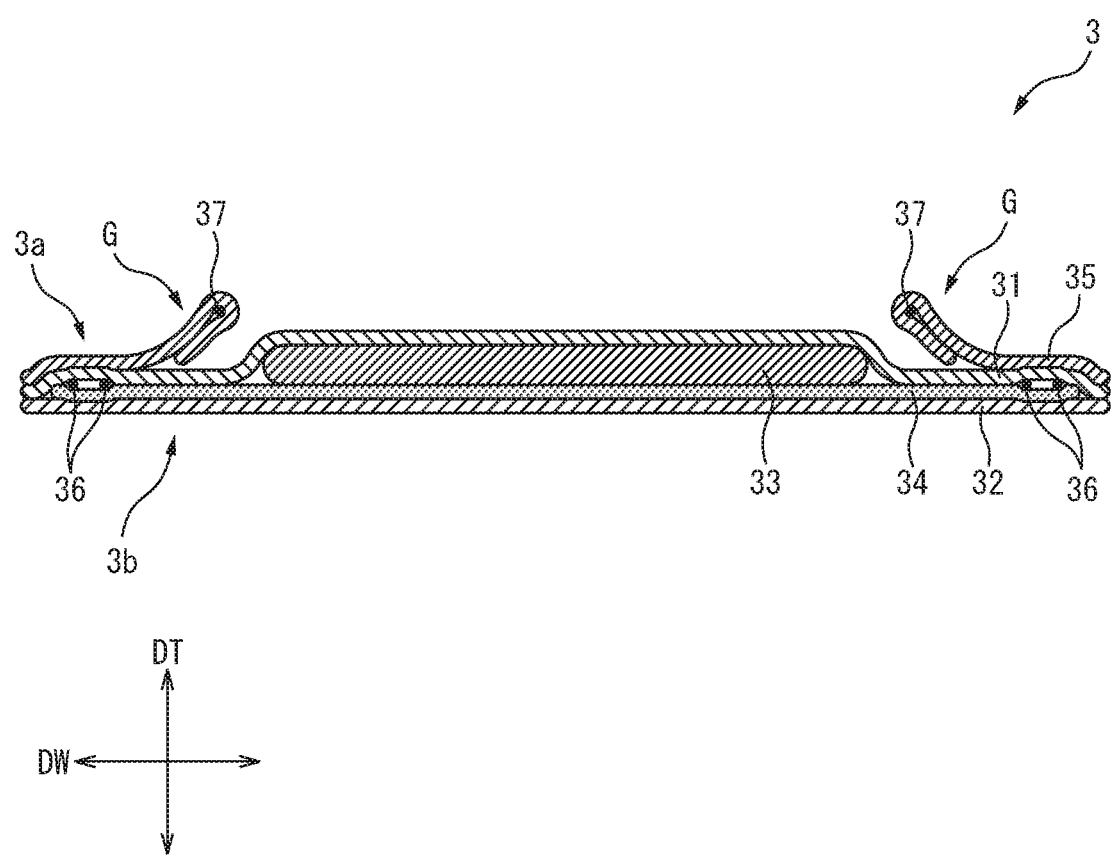
FIG. 3 is a cross-sectional view of the disposable diaper 1 for a pet along line of FIG. 2.
Figure 5:
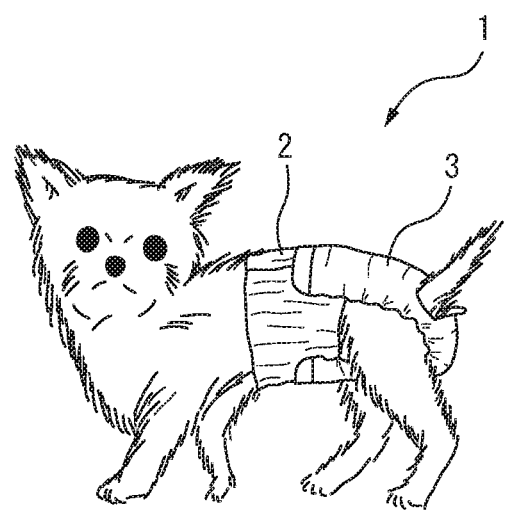
FIG. 5 is a schematic diagram showing the disposable diaper 1 for a pet when fitted onto a dog.

FIG. 1 is a perspective view of the disposable diaper 1 for a pet (absorbent article for an animal) according to an embodiment of the invention, FIG. 2 is a plan view of the disposable diaper 1 for a pet in the expanded state, and FIG. 3 is a cross-sectional view of the disposable diaper 1 for a pet along line III-III of FIG. 2. FIG. 5 is a schematic diagram showing the disposable diaper 1 for a pet in the state fitted onto a female dog.

As shown in FIG. 1, FIG. 2 and FIG. 5, the disposable diaper 1 for a pet according to this embodiment has a 2-piece structure comprising a support section 2 fitted in a freely detachable manner along the region around the torso including the dorsal region and abdominal region of a pet such as a dog that is to be fitted (a female dog for this embodiment), and having a torso-facing surface 2a facing the region around the torso of the pet and a non-torso-facing surface 2b located on the opposite side from the torso-facing surface 2a, and an absorbing body section 3 disposed along the dorsal region, lower crotch region and abdominal region of the pet, wherein both end sections, i.e. the dorsal region side end section $3E_1$ located on the dorsal region side of the pet and the abdominal region side end section $3E_2$ located on the abdominal region side of the pet, are each engaged and fastened in a freely detachable manner with respect to the non-torso-facing surface 2b of the support section 2.

In the disposable diaper 1 for a pet, the support section 2 is a member fitted in a freely detachable manner along the region around the torso including the dorsal region and abdominal region of the pet, serving to support the absorbing body section 3 that is engaged and fastened with the non-torso-facing surface 2b of the support section 2, so that it does not become dislocated or slip off. The absorbing body section 3, on the other hand, is a member disposed along the dorsal region, lower crotch region and abdominal region of the pet, and particularly in the lower crotch region of the pet, and serving to absorb and hold excreta such as urine discharged from a pet.

Moreover, as shown in FIG. 2, the absorbing body section 3 has a longitudinal shape with a lengthwise direction DL and a widthwise direction DW in the planar view when in the expanded state, and has a first surface 3a that faces the pet when the disposable diaper 1 for a pet is fitted on the pet and a second surface 3b on the side opposite from the first surface 3a, the absorbing body section 3 also comprising engagement sections 38 disposed on the first surface 3a respectively at both end sections, i.e. the dorsal region side end section $3E_1$ and the abdominal region side end section $3E_2$ located at both ends in the lengthwise direction DL of the absorbing body section 3, in the planar view when in the expanded state, an absorbent body 33 disposed so that it extends in the lengthwise direction DL in a manner straddling the center axis line $C_W$ running in the widthwise direction DW of the absorbing body section 3 and extends in the widthwise direction DW in a manner straddling the center axis line $C_L$ running in the lengthwise direction DL, which absorbs and holds excreta, a tail opening 39 for insertion of the tail of the pet, formed between the absorbent body 33 and the dorsal region side end section $3E_1$, and elastic members 36 made of elastic yarn, to impart contractive force in the lengthwise direction DL of the absorbing body section 3. In addition, the elastic members 36 are disposed respectively on both outer sides in the widthwise direction DW of the absorbent body 33, and have lengths in the lengthwise direction that are at least longer than the length in the lengthwise direction of the absorbent body 33.

Since in the disposable diaper 1 for a pet of this embodiment having the construction described above, the absorbing body section 3 comprises engagement sections 38 disposed on the first surface 3a respectively at both end sections, i.e. the dorsal region side end section $3E_1$ and the abdominal region side end section $3E_2$ located at both ends in the lengthwise direction DL of the absorbing body section 3, a tail opening 39 formed between the absorbent body 33 and the dorsal region side end section $3E_1$, and elastic members 36 disposed respectively at both outer sides in the widthwise direction DW of the absorbent body 33 and having lengths in the lengthwise direction that are at least longer than the length in the lengthwise direction of the absorbent body 33, which impart contractive force in the lengthwise direction DL of the absorbing body section 3, when the tail of the pet has been inserted through the tail opening 39 to fit the disposable diaper 1 for a pet onto the body of the pet, contractive force of the elastic members 36 acting between the dorsal region side end section $3E_1$ and tail opening 39 and between the abdominal region side end section $3E_2$ and tail opening 39 of the absorbing body section 3 causes the engagement sections 38 of the absorbing body section 3 to be pulled along the body surface of the pet and toward the tail opening 39 that has a fixed location due to the tail of the pet, such that force in the direction crossing with the girth direction of the pet (shearing force) acts on the section where the engagement sections 38 of the absorbing body section 3 and the non-torso-facing surface 2b of the support section 2 are engaged, thus strengthening engagement between the engagement sections 38 of the absorbing body section 3 and the non-torso-facing surface 2b of the support section 2 and rendering the absorbing body section 3 less likely to detach from the support section 2.

Moreover, when the disposable diaper 1 for a pet of this embodiment is fitted onto the body of a pet, since the lower crotch region-facing section of the absorbing body section 3 is pulled relatively toward the abdominal region side end section $3E_2$ and the tail opening 39, respectively, due to the contractive force of the elastic members 36 acting between the abdominal region side end section $3E_2$ and the tail opening 39 of the absorbing body section 3, the lower crotch region-facing section more easily comes into contact with the lower crotch region of the pet (i.e., a gap is less likely to form between the body surface of the pet and the surface of the absorbing body section 3). Moreover, in the absorbing body section 3, since the regions on both outer sides in the widthwise direction DW of the absorbent body 33 are the regions corresponding to the leg-surrounding regions of the pet, placement of the elastic members 36 in these regions facilitates elastic deformation of the regions to follow movement of the leg-surrounding regions of the pet, and allows the regions to be fitted more exactly and persistently to the lower crotch region of the pet even during movement by the pet, such as walking.

Therefore, the disposable diaper 1 for a pet of this embodiment can prevent leakage of excreta by the animal, by being unlikely to detach from the body of the animal and by exactly fitting to the lower crotch region of the pet.

The "animal" to which the absorbent article for an animal according to the invention is to be applied is not particularly restricted so long as it is an animal that can be reared, such as a pet, and it may be an animal such as a dog, as exemplified by this embodiment, or a cat or monkey.

According to the invention, the "excreta" to be absorbed and held by the absorbent article for an animal are not particularly restricted so long as they can be absorbed and held in the absorbent body described below, and for example, they may be various types of liquid to low-viscosity body fluids such as urine or feces, or blood.

Each of the members composing the disposable diaper 1 for a pet of this embodiment will now be described in greater detail.

<Support Section>

According to this embodiment, as shown in FIG. 5, the support section 2 is a member fitted in a freely detachable manner along the region around the torso including the dorsal region and abdominal region of the pet, to support the absorbing body section 3 that is to be engaged and fastened with the non-torso-facing surface 2b of the support section 2, and when it is fitted onto the pet, as shown in FIG. 1 and FIG. 5, the torso-facing surface 2a facing the region around the torso of the pet and the non-torso-facing surface 2b located on the side opposite from the torso-facing surface 2a have a tubular structure running in the direction along the head (front end) and tail (rear end) of the pet (i.e., the front-back direction), and running around the torso of the pet.

Incidentally, throughout the present description, the "surface on the relatively proximal side with respect to the body surface around the torso of an animal that is to be fitted, in the thickness direction DT of the support section" will be referred to as the "torso-facing surface", and the "surface on the relatively distal side with respect to the body surface around the torso of an animal that is to be fitted, in the thickness direction DT of the support section" will be referred to as the "non-torso-facing surface".

For this embodiment, as shown in FIG. 2, the support section 2 has a first direction $D_1$ corresponding to the girth direction of the pet, in the planar view when in the expanded state, and a second direction $D_2$ orthogonal to the first direction $D_1$, while being composed of a single sheet-like member 21 having the aforementioned torso-facing surface 2a as the surface facing the region around the torso of the pet when it is fitted onto the pet, and the aforementioned non-torso-facing surface 2b located on the opposite side from the torso-facing surface 2a. Furthermore, the sheet-like member 21 has, on the torso-facing surface 2a of one end section $2E_1$ among both end sections in the first direction $D_1$, a first engagement section 23 for the support section (support section engagement section) that is able to engage with any portion of the non-torso-facing surface 2b of the support section 2. Since the first engagement section 23 for the support section can engage with any portion of the non-torso-facing surface 2b of the support section 2, the disposable diaper 1 for a pet of this embodiment can match the support section 2 to the size of the girth of the pet for exact fitting, and it is possible to effectively prevent dislocation or slipping off of the disposable diaper 1 for a pet including the support section 2, and therefore the absorbing body section 3, from the body of the pet.

For the absorbent article for an animal of the invention, the construction of the support section is not limited to the construction of this embodiment, and for example, the support section may have a tubular construction wherein the torso-facing surface facing the region around the torso of the animal and the non-torso-facing surface located on the side opposite the torso-facing surface run in the direction along the head (the front end) and the tail (rear end) of the animal (i.e., in the front-back direction), while also running continuously without a seam in the girth direction of the pet. If the support section has such a construction, then in order to closely fit the support section around the torso of the animal, preferably it is stretchable in the girth direction of the animal, or it has a construction that causes contraction of the circumference in the girth direction of the support section (for example, an adjustor).

Furthermore, according to this embodiment, the support section 2 has, on the non-torso-facing surface 2b of the other end section $2E_2$ among both end sections in the first direction $D_1$, a second engagement section 24 for the support section that is able to engage with any portion of the torso-facing surface 2a of the support section 2. Since the second engagement section 24 for the support section can engage with any portion of the torso-facing surface 2a of the support section 2, the disposable diaper 1 for a pet of this embodiment can match the support section 2 to the size of the girth of the pet for more exact fitting, and it is possible to more effectively prevent dislocation or slipping off of the disposable diaper 1 for a pet including the support section 2, and thus the absorbing body section 3, from the body of the pet. Furthermore, if the support section 2 comprises a second engagement section 24 for the support section, then when the support section 2 has been fitted on a pet, on the inner side of the support section (i.e., the pet side), the end section $2E_2$ at the other end in the first direction $D_1$ of the sheet-like member 21 will become engaged and fastened with the torso-facing surface 2a of the support section 2 by the second engagement section 24 for the support section, helping to prevent bending or crimping of the end section $2E_2$ at the other end, and making it less likely to create the feeling of an extraneous object or a feeling of discomfort for the pet wearing the support section 2.

For this embodiment, the sheet-like member 21 composing the support section 2 is constructed of a layered nonwoven fabric in which two nonwoven fabrics are layered, and as shown in FIG. 2, the elastic members 22 for the support section comprising multiple elastic yarns, extending in the first direction $D_1$ and aligned in the second direction $D_2$, are disposed between the two nonwoven fabrics. The elastic members 22 for the support section are fixed by a hot-melt adhesive to the two nonwoven fabrics. Stretching action of the elastic members 22 for the support section causes the support section 2 to exhibit stretchability in the first direction $D_1$, which is the direction around the torso of the pet when it is fitted onto the pet. If the support section 2 is thus stretchable in the girth direction of the pet, force in the direction crossing with the girth direction of the pet (shearing force), especially when the pet has moved, acts more powerfully at the portions where the engagement sections of the absorbing body section 3 and the non-torso-facing surface 2b of the support section 2 have engaged, thus producing more firm engagement between the engagement sections of the absorbing body section 3 and the non-torso-facing surface 2b of the support section 2. This makes the absorbing body section 3 even less likely to detach from the support section 2.

In addition, since the support section 2 can be more exactly fitted to the region around the torso of the pet if the support section 2 is stretchable in the girth direction of the pet, it is possible to prevent dislocation or slipping off of the support section 2, and thus the disposable diaper 1 for a pet, from the body of the pet.

For this embodiment, the sheet-like member 21 composing the support section 2 is formed of two nonwoven fabrics and elastic members 22 for the support section disposed between them; however, according to the invention there is no limitation to this aspect, and for example, the sheet-like member may be a sheet-like member formed of at least two sheets such as woven fabrics or knitted fabrics and elastic members for the support section disposed between them, or a sheet-like member formed of at least one non-stretchable sheet or stretchable sheet (for example, a stretchable nonwoven fabric) alone, or a non-stretchable sheet-like member obtained by layering a plurality of woven fabrics or knitted fabrics. Even when the support section has a tubular structure running continuously without a seam in the girth direction of the pet as described above, the support section may likewise be, for example, a tubular sheet-like member composed of at least two sheets such as nonwoven fabrics or woven fabrics or knitted fabrics, and elastic members for the support sections disposed between them, or a tubular sheet-like member composed of at least one stretchable sheet (for example, a stretchable nonwoven fabric) alone.

According to the invention, the means for imparting stretchability to the sheet-like member composing the support section in the first direction (the girth direction of the animal) is not particularly restricted, and instead of the aforementioned elastic yarn, it is possible to employ any desired stretchability-imparting means such as a belt-shaped stretchable sheet, or slits formed in the sheet-like member, for example. When elastic members are used as stretchability-imparting means, the elastic members are not particularly limited so long as they are materials capable of elongation and contraction, and they may be rubber threads or flat rubber made of natural rubber; or filamentous or belt-shaped molded thermoplastic elastomers such as urethane or ethylene-vinyl acetate copolymer (EVA).

For this embodiment, the specific engaging means for the first engagement section 23 for the support section (support section engagement section) provided on the sheet-like member 21 composing the support section 2 is not particularly limited, and any desired engaging means may be employed such as a mechanical fastener comprising a hook section material and a loop section material, for example, but preferably the support section engagement section employs the same engaging means for each engagement section 38 of the absorbing body section 3 described below, or in other words, engaging means constructed from a plurality of engaging protrusions each having a shaft portion running from the surface of the sheet-like member facing the region around the torso, and a wide portion running in the direction in which the outer peripheral surface of the shaft portion widens, at the tip of the shaft portion. If the support section engagement section is constructed from a plurality of engaging protrusions each having such a specified structure, then the plurality of engaging protrusions will be able to engage with any desired fiber structure such as a nonwoven fabric, thereby eliminating the need to separately provide a loop structure that is able to engage with the plurality of engaging protrusions, on the non-girth-facing surface of the support section where the support section engagement section engages, and also allowing the location where the end section $2E_1$ on one end in the first direction $D_1$ of the sheet-like member is engaged and fastened to be adjusted as desired.

Incidentally, according to the invention, the means for joining the end section at one end in the first direction $D_1$ of the sheet-like member composing the support section to the surface of the sheet-like member that is not facing the region around the torso is not limited to the support section engagement section of the embodiment described above, and the joining means may be an adhesive section formed by providing a pressure-sensitive adhesive, for example, but it is preferred to use engaging means according to this embodiment for the joining means described above, from the viewpoint of helping to prevent detachment of the joining (i.e., detachment of the support section from the body of the animal) even if the inner diameter of the tubular structure of the support section has been altered when the animal wearing the support section has moved.

<Absorbing Body Section>

According to this embodiment, as shown in FIG. 5, the absorbing body section 3 is a member disposed along the dorsal region, lower crotch region and abdominal region of the pet, and particularly in the lower crotch region of the pet, and serving to absorb and hold excreta such as urine discharged from a pet. As shown in FIG. 1 and FIG. 5, the absorbing body section 3 is used with both end sections, i.e. the dorsal region side end section $3E_1$ located on the dorsal region side of the pet and the abdominal region side end section $3E_2$ located on the abdominal region side of the pet, being engaged and fastened in a freely detachable manner with respect to the non-torso-facing surface 2b of the support section 2.

Also according to this embodiment, as shown in FIG. 2, the absorbing body section 3 has a longitudinal outer shape that is essentially rectangular, with a lengthwise direction DL and a widthwise direction DW in the planar view when in the expanded state, while also having a first surface 3a that is the surface facing the pet when the disposable diaper 1 for a pet is fitted onto the body of the pet, and a second surface 3b that is the surface on the opposite side from the first surface 3a. In addition, the absorbing body section 3 comprises engagement sections 38 disposed on the first surface 3a respectively at both end sections, i.e. the dorsal region side end section $3E_1$ and the abdominal region side end section $3E_2$ located at both ends in the lengthwise direction DL of the absorbing body section 3, in the planar view when in the expanded state, an absorbent body 33 disposed so that it extends in the lengthwise direction DL in a manner straddling the center axis line $C_W$ running in the widthwise direction DW of the absorbing body section 3 and extends in the widthwise direction DW in a manner straddling the center axis line $C_L$ running in the lengthwise direction DL, and elastic members 36 that impart contractive force in the lengthwise direction DL of the absorbing body section 3. In addition, as shown in FIG. 2, the elastic members 36 are disposed respectively on both outer sides in the widthwise direction DW of the absorbent body 33, and have lengths in the lengthwise direction that are at least longer than the length in the lengthwise direction of the absorbent body 33.

In addition, on the center axis line $C_L$ running in the lengthwise direction DL of the absorbing body section 3, a tail opening 39 through which the tail of the pet is inserted is formed at a location between the absorbent body 33 and the dorsal region side end section $3E_1$, and closer to the dorsal region side end section $3E_1$ in the lengthwise direction DL (closer to the lower side in FIG. 2).

According to the invention, the outer shape of the absorbing body section in the planar view is not limited to such a longitudinal shape that is essentially rectangular, and so long as the shape is a longitudinal shape such that the length dimension in the lengthwise direction DL is longer than the width dimension in the widthwise direction DW, any longitudinal shape (for example, rectangular, elliptical or gourd-shaped) may be employed according to the particular purpose of use or the body type of the animal.

According to this embodiment, since the absorbing body section 3 comprises elastic members 36 disposed at both outer sides in the widthwise direction DW of the absorbent body 33 and having lengths in the lengthwise direction that are at least longer than the length in the lengthwise direction of the absorbent body 33, when the tail of the pet has been inserted through the tail opening 39 to fit the disposable diaper 1 for a pet onto the body of the pet, the contractive force of the elastic members 36 acting between the dorsal region side end section $3E_1$ and tail opening 39 and between the abdominal region side end section $3E_2$ and tail opening 39 of the absorbing body section 3 causes the engagement sections 38 of the absorbing body section 3 to be pulled along the body surface of the pet and toward the tail opening 39 that has a fixed location due to the tail of the pet, such that force in the direction crossing with the girth direction of the pet (shearing force) acts on the section where the engagement sections 38 of the absorbing body section 3 and the non-torso-facing surface $2b$ of the support section 2 are engaged, thus strengthening engagement between the engagement sections 38 of the absorbing body section 3 and the non-torso-facing surface $2b$ of the support section 2 and rendering the absorbing body section 3 less likely to detach from the support section 2. Moreover, since the lower crotch region-facing section of the absorbing body section 3 is relatively pulled toward the abdominal region side end section $3E_2$ and the tail opening 39, respectively, due to the contractive force of the elastic members 36 acting between the abdominal region side end section $3E_2$ and the tail opening 39 of the absorbing body section 3, the lower crotch region-facing section more easily comes into contact with the lower crotch region of the pet (i.e., a gap is less likely to form between the body surface of the pet and the surface of the absorbing body section 3).

In addition, since the elastic members 36 of the absorbing body section 3 are disposed in the regions on both outer sides in the widthwise direction DW of the absorbent body 33 which are the regions corresponding to the leg-surrounding regions of the pet, the regions where the elastic members 36 are disposed facilitate elastic deformation of those regions to follow movement of the leg-surrounding regions of the pet, and allow the regions to be fitted more exactly and persistently to the lower crotch region of the pet even during movement by the pet, such as walking.

According to this embodiment, the absorbing body section 3 is composed of a laminated body having, in its thickness direction DT, a liquid-permeable top sheet 31 located on the first surface $3a$ side, a liquid-impermeable back sheet 32 located on the second surface $3b$ side, an absorbent body 33 disposed between both sheets, a pair of side sheets 35 located on the first surface $3a$ side of the top sheet 31, and an optional back film 34 disposed between the back sheet 32 and the absorbent body 33.

Each of the members composing the absorbing body section 3 in the disposable diaper 1 for a pet of this embodiment will now be described in greater detail.
(Top Sheet)

For this embodiment, as shown in FIG. 2 and FIG. 3, the top sheet 31 is composed of a nonwoven fabric having liquid permeability, disposed at a location of the first surface $3a$ side of the absorbing body section 3 that is able to directly contact with the body of the pet on which it is to be fitted. According to the invention, the nonwoven fabric composing the top sheet is not particularly restricted so long as it has liquid permeability, and for example, any desired nonwoven fabric may be used, such as a spunlace nonwoven fabric, air-through nonwoven fabric, spunbond nonwoven fabric, point bond nonwoven fabric or meltblown nonwoven fabric, or a combination thereof (for example, an SMS nonwoven fabric). The structure of the nonwoven fabric composing the top sheet is also not particularly restricted, and the nonwoven fabric used may be a flat, nonporous nonwoven fabric, or it may be a porous nonwoven fabric or a nonwoven fabric having a protrusion-recess structure (a protrusion-recess structure with an undulating cross-section or ridge-furrow structure).

The type of fibers used in a nonwoven fabric composing the top sheet is also not particularly restricted, and examples include cellulosic fibers; and thermoplastic resin fibers of an olefin-based resin or polyester-based resin, any of which may be used alone or in combinations of two of more different types of fibers. Incidentally, the basis weight of a nonwoven fabric composing the top sheet is not particularly restricted so long as it does not inhibit the liquid permeability, and it is in the range of 6 $g/m^2$ to 50 $g/m^2$, for example.
(Back Sheet)

For this embodiment, as shown in FIG. 2 and FIG. 3, the back sheet 32 is disposed at a location on the second surface $3b$ side that is on the opposite side of the absorbing body section 3 from the top sheet 31, and it is composed of a liquid-impermeable sheet that functions to prevent permeation of excreta such as urine that has been discharged from the pet on which it has been fitted. According to the invention, the liquid-impermeable sheet composing the back sheet is not particularly restricted so long as it can prevent permeation of excreta such as urine that has been discharged from an animal, and for example, a hydrophobic nonwoven fabric, SMS layered nonwoven fabric, liquid-impermeable plastic film, or a laminated sheet comprising any desired combination of these sheets, may be used.
(Absorbent Body)

For this embodiment, as shown in FIG. 2 and FIG. 3, the absorbent body 33 is disposed between the top sheet 31 and the back sheet 32 and is composed of a water absorbing member that absorbs and holds excreta such as urine that has permeated the top sheet 31. Moreover, for this embodiment, as shown in FIG. 2, the absorbent body 33 has a long outer shape in the lengthwise direction DL, disposed so that it extends in the lengthwise direction DL in a manner straddling the center axis line $C_W$ running in the widthwise direction DW of the absorbing body section 3, and extends in the widthwise direction DW in a manner straddling the center axis line $C_L$ running in the lengthwise direction DL, in the planar view when in the expanded state, with the approximate center section in the lengthwise direction DL having an essentially hourglass shape that is narrowed toward the inner side in the widthwise direction DW. According to the invention, the outer shape of the absorbent body section in the planar view is not limited to such a longitudinal shape that is essentially hourglass-shaped, and so long as the shape is a longitudinal shape such that the length dimension in the lengthwise direction DL is longer than the width dimension in the widthwise direction DW, any longitudinal shape (for example, rectangular or elliptical) may be employed according to the particular purpose of use or the body type of the animal.

The water absorbing member composing the absorbent body of the invention is not particularly restricted so long as it absorbs and retains excreta such as urine that has been discharged from an animal, and any water absorbing member known in the relevant field may be used. Examples of such water absorbing members include those having an absorbent core formed of an absorbent material, covered with a hydrophilic core wrap sheet such as a tissue. The absorbent material composing the absorbent core may also be, for example, hydrophilic fibers or a superabsorbent polymer, and specifically, cellulose fibers such as fluff pulp or cotton; regenerated cellulose fibers such as rayon or fibril rayon; semi-synthetic cellulose fibers such as acetate or triacetate; hydrophilicized thermoplastic hydrophobic chemical fibers; granules composed of a superabsorbent polymer such as sodium acrylate copolymer; or a combination of any two or more of these.

(Elastic Members)

For this embodiment, as shown in FIG. 2, the elastic members 36 that impart contractive force to the absorbing body section 3 in the lengthwise direction DL are constructed with 4 elastic yarns, being disposed with two each on both outer sides in the widthwise direction DW of the absorbent body 33, and having lengths in the lengthwise direction that are at least longer than the length of the absorbent body 33 in the lengthwise direction. According to the invention, incidentally, the number of elastic members disposed on each of both outer sides in the widthwise direction of the absorbent body is not limited to the embodiment described above so long as the effect of the invention can be exhibited, and for example, the elastic members may be disposed with one each, or disposed with 3 or more each, on both outer sides in the widthwise direction of the absorbent body.

According to the invention, the elastic members that impart contractive force to the absorbing body section in the lengthwise direction are not particularly restricted so long as they are made of a material that can impart contractive force to the absorbing body section in the lengthwise direction when in the expanded state, and for example, any elastic members such as rubber threads or flat rubber made of natural rubber; or filamentous or belt-shaped molded thermoplastic elastomers such as urethane or ethylene-vinyl acetate copolymer (EVA), may be used.

(Side Sheets)

For this embodiment, as shown in FIG. 2 and FIG. 3, the pair of side sheets 35 are formed of long belt-shaped sheet members in the lengthwise direction DL, in the planar view, and are disposed on the surface of the first surface 3a side of the top sheet 31, at both end sections in the widthwise direction DW. The pair of side sheets 35 are joined to the end sections running in the lengthwise direction DL located on the outer sides in the widthwise direction DW, and both end sections in the lengthwise direction DL are joined to the surface on the first surface 3a side of the top sheet 31. Therefore, as shown in FIG. 3, the pair of side sheets 35 have fixed edges as the end sections running in the lengthwise direction DL located on the outer sides in the widthwise direction DW, while the end sections located on the inner side in the widthwise direction DW are free edges.

Also, as shown in FIG. 2 and FIG. 3, each of the end sections of the pair of side sheets 35 located on the inner side in the widthwise direction DW is folded toward the top sheet 31 side, and gather elastic members 37 running in the lengthwise direction DL are disposed in a manner enveloped by the folded end sections. Contraction of the gather elastic members 37 causes the pair of side sheets 35 to rise from the top sheet 31 side, allowing formation of three-dimensional gathers G, as shown in FIG. 1 and FIG. 3.

In the disposable diaper 1 for a pet of this embodiment, such three-dimensional gathers G function as anti-leakage walls, such that excreta such as urine that has been discharged by the pet are less likely to leak any further from the absorbing body section 3.

According to the invention, the side sheets are not particularly restricted so long as they can function as anti-leakage walls when the three-dimensional gathers are formed, and for example, it may be composed of a water-repellent or hydrophobic nonwoven fabric. Also according to the invention, the nonwoven fabric that may be used to form the side sheets is not particularly restricted, and it may be any of various nonwoven fabrics such as, for example, a spunlace nonwoven fabric, spunbonded nonwoven fabric, thermal bonded nonwoven fabric, meltblown nonwoven fabric or air-through nonwoven fabric. The fibers composing the nonwoven fabric are not particularly restricted, and for example, synthetic fibers such as polyolefin-based fibers, polyester-based fibers or polyamide-based fibers, or cellulosic fibers such as rayon or cotton, may be used.

The same material used for the elastic members described above may also be used for the gather elastic members.

(Engagement Section)

According to this embodiment, as shown in FIG. 2, the engagement sections 38 of the absorbing body section 3 are disposed on the first surface 3a, at both end sections, i.e. the dorsal region side end section $3E_1$ and the abdominal region side end section $3E_2$, located at both ends in the lengthwise direction DL of the absorbing body section 3, in the planar view when in the expanded state, and they are oblong, having essentially rectangular outer shapes running in the widthwise direction DW of the absorbing body section 3. The engagement sections 38 disposed on the dorsal region side end section $3E_1$ and abdominal region side end section $3E_2$, respectively, located at both ends in the lengthwise direction DL of the absorbing body section 3, are each engaged and fastened with the non-torso-facing surface 2b of the support section 2 when the absorbing body section 3 is fitted onto the pet on which the support section 2 has already been fitted. When the support section 2 and absorbing body section 3 (i.e., the disposable diaper 1 for a pet) is fitted onto the body of a pet in this manner, the contractive force of the elastic members 36 acting between the dorsal region side end section $3E_1$ and tail opening 39 and between the abdominal region side end section $3E_2$ and tail opening 39 of the absorbing body section 3 causes each engagement section 38 (i.e. the engagement section 38 disposed on the dorsal region side end section $3E_1$ and the engagement section 38 disposed on the abdominal region side end section $3E_2$) to be pulled along the body surface of the pet and toward the tail opening 39 that has a fixed location due to the tail of the pet, such that force in the direction crossing with the girth direction of the pet (shearing force) acts on the section where each engagement section 38 of the absorbing body section 3 and the non-torso-facing surface 2b of the support section 2 are engaged, thus strengthening engagement between the engagement sections 38 of the absorbing body section 3 and the non-torso-facing surface 2b of the support section 2 and rendering the absorbing body section 3 less likely to detach from the support section 2.

Figure 4A:
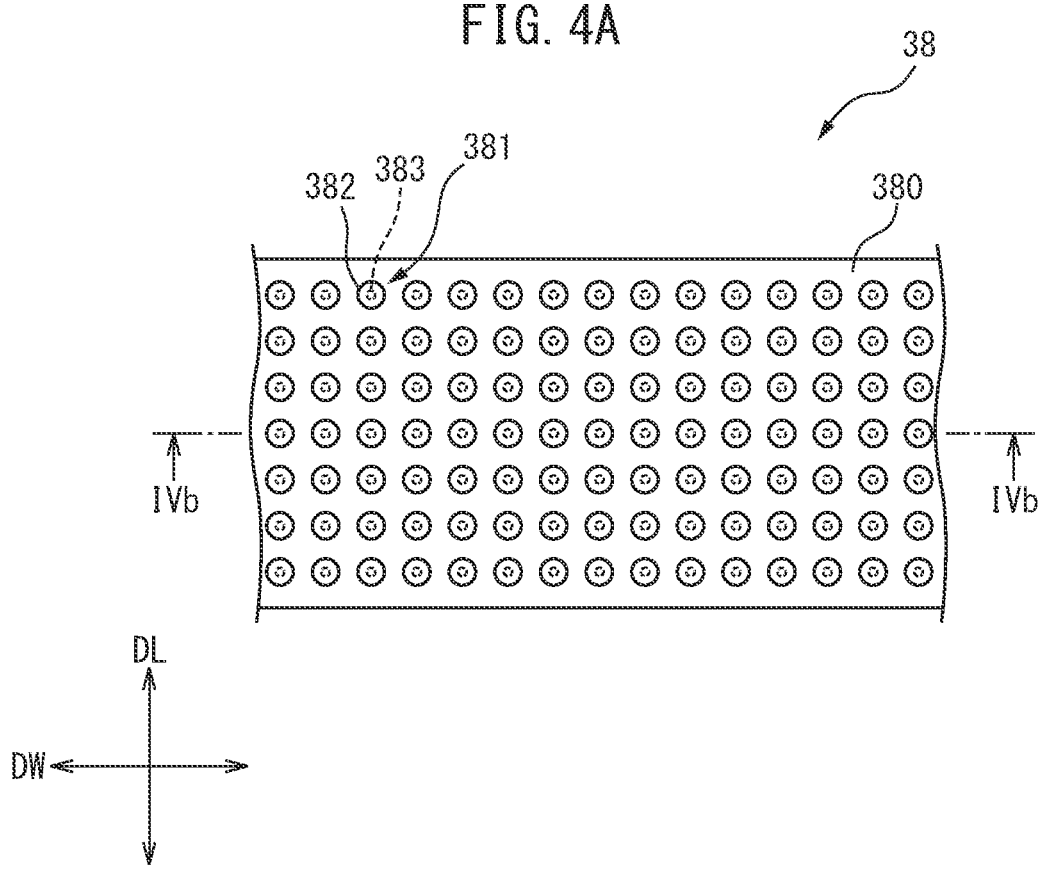
FIG. 4A is an enlarged plan view of the main part of an engagement section 38 of the disposable diaper 1 for a pet in region IV of FIG. 2.

According to the invention, the specific engaging means for the engagement sections of the absorbing body section is not particularly restricted, and any engaging means may be employed such as a mechanical fastener comprising a hook section material and a loop section material, for example, but preferably the same engaging means is used as for the engagement sections 38 of this embodiment, as described in detail below. FIG. 4A is an enlarged plan view of the main part of an engagement section 38 of the disposable diaper 1 for a pet according to this embodiment, in region IV of FIG. 2, and FIG. 4B is a cross-sectional view of the same along line IVb-IVb of FIG. 4A.

Figure 4B:
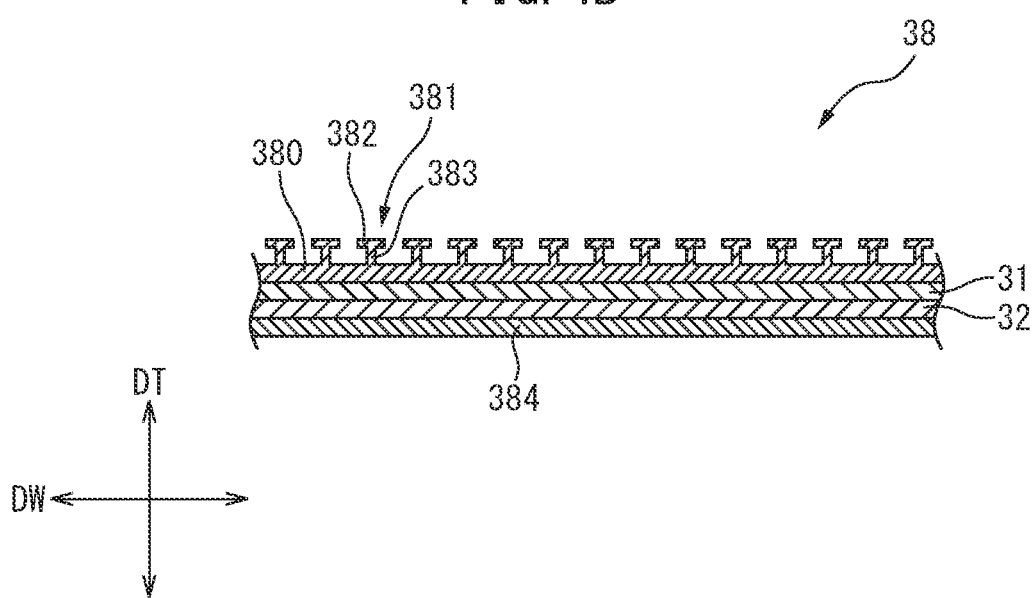
FIG. 4B is a cross-sectional view of the same along line IVb-IVb of FIG. 4A.

According to this embodiment, as shown in FIG. 4A and FIG. 4B, the engagement section 38 of the absorbing body section 3 has a base 380 disposed on the first surface 3a of the absorbing body section 3, and a plurality of engaging protrusions 381 protruding from the base 380, each of the plurality of engaging protrusions 381 having a shaft portion 383 that runs from the first surface 3a of the absorbing body section 3 (specifically, the base 380), and a wide portion 382 that runs in the direction in which the outer peripheral surface of the shaft portion 383 widens, at the tip of the shaft portion 383. With an engagement section 38 having such a construction, when the engagement section 38 has been engaged and fastened with the non-torso-facing surface 2b of the support section 2, the engagement section 38 can respond to forces in different directions on the non-torso-facing surface 2b of the support section 2 even when the engagement section 38 has been pulled in different directions by movement of the pet, making it able to engage with the non-torso-facing surface 2b of the support section 2, so that the engagement between the engagement section 38 of the absorbing body section 3 and the non-torso-facing surface 2b of the support section 2 can be maintained in a firm state. The absorbing body section 3 in the disposable diaper 1 for a pet of this embodiment will thus be even less likely to detach from the support section 2.

Moreover, if the engagement sections 38 of the absorbing body section 3 are composed of engaging protrusions 381 having the aforementioned specific structure, the engaging protrusions 381 can engage with a desired fiber structure such as a nonwoven fabric, thus eliminating the need to provide a loop structure that is engageable with the engaging protrusions 381, on the non-torso-facing surface 2b of the support section 2 where the engagement sections 38 engage, and allowing the absorbing body section to be constructed with any arbitrary adjustable location where it may be engaged and fastened with the support section 2. This will allow the disposable diaper 1 for a pet of this embodiment to be worn with the lower crotch region-facing section of the absorbing body section 3 more exactly fitting the lower crotch region of the pet.

The disposable diaper 1 for a pet of this embodiment can therefore more stably and reliably prevent leakage of excreta of the pet.

According to the invention, the structure of the engagement sections 38 of the absorbing body section 3 is not limited to the structure of this embodiment, and for example, the structures of the wide portions of the engagement sections may have any desired spatial structure such as spherical or conical.

According to the invention, the location where the engagement section of the absorbing body section is disposed is not limited to the location for this embodiment, and for example, the engagement section may be disposed on the first surface at one end section among the dorsal region side end section and the abdominal region side end section located at both ends in the lengthwise direction of the absorbing body section, in the planar view when in the expanded state, and it may also be partially disposed in the widthwise direction of the end section. Incidentally, when the engagement section is disposed on the first surface at one end section among the dorsal region side end section and the abdominal region side end section located at both ends in the lengthwise direction of the absorbing body section, in the planar view when in the expanded state, the other end section is joined and fixed to the non-facing surface of the support section around the torso by any desired joining means other than engagement.

According to the invention, the engagement section of the absorbing body section preferably at least partially has a non-stretchable portion. If the engagement section of the absorbing body section has such a non-stretchable portion, since the non-stretchable portion is resistant to structural deformation even with application of force, it is possible to more stably maintain engagement with the non-girth-facing surface of the support section at the non-stretchable portion, and to further minimize detachment of the absorbing body section from the support section. The means for providing non-stretchable portion at the engagement section of the absorbing body section may be avoiding placement of the elastic member at the engagement section as in the embodiment described above (see FIG. 2), or placement of a non-stretchable sheet or the like, described below, at the location corresponding to the engagement section in the thickness direction, on the second surface of the absorbing body section.

Also, when the absorbing body section is composed of a laminated body that includes, in the thickness direction DT, at least a liquid-permeable top sheet, a liquid-impermeable back sheet, an absorbent body disposed between both of these sheets, and a pair of side sheets located on the first surface side of the top sheet, and the laminated body has a border section with a different number of layers in the widthwise direction, in the planar view with the absorbing body section in the expanded state, the engagement section of the absorbing body section is preferably disposed so that it extends in the widthwise direction straddling at least the border section. For the embodiment described above, as shown in FIG. 2, the engagement sections 38 are disposed at both end sections 3E$_1$, 3E$_2$ in the lengthwise direction DL, in the planar view when the absorbing body section 3 is in the expanded state, straddling the border sections between both end sections in the widthwise direction DW where the side sheets 35 are disposed (i.e., the portions with 3 layers comprising the side sheets 35, top sheet 31 and back sheet 32), and the center section where the side sheets 35 are not disposed (i.e., the portion with only 2 layers comprising the top sheet 31 and back sheet 32) (the border sections being the inner edge sections in the widthwise direction DW of the side sheets 35, running in the lengthwise direction DL), in the widthwise direction DW.

Since the border section with a different number of layers for the laminated body is the section at a point where the rigidity changes, deformation or tearing of the absorbing body section tends to occur from the border section as an origin, but if the engagement section is disposed straddling such a border section, then when the engagement section has been engaged and fastened with the non-torso-facing surface of the support section, the section that tends to undergo deformation or tearing will also be engaged and fastened at the support section, and therefore deformation or tearing of the absorbing body section from the border section as an origin will be less likely to occur. It is therefore possible for the absorbent article for an animal, having such a construction, to more stably and reliably prevent leakage of excreta of the animal.

Moreover, since the border section with a different number of layers for the laminated body is also the section that is susceptible to crimping of the members composing the absorbing body section, due to movement such as walking or scratching behavior by the animal, placement of the engagement section in a manner straddling the border section as described above can help minimize crimping of the members composing the absorbing body section.

Furthermore, according to the invention, the engagement section of the absorbing body section is preferably disposed in the region that include an edge in the lengthwise direction of the absorbing body section, on the first surface on at least one end section among the dorsal region side end section and abdominal region side end section located at both ends in the lengthwise direction of the absorbing body section. Incidentally, for this embodiment as shown in FIG. 2, the engagement sections 38 of the absorbing body section 3 are disposed in the regions including the edges $3e_1$ and $3e_2$ in the lengthwise direction DL of the absorbing body section 3, on the first surface $3a$ at both end sections, i.e. the dorsal region side end section $3E_1$ and the abdominal region side end section $3E_2$, located at both ends in the lengthwise direction DL of the absorbing body section 3.

If the engagement section of the absorbing body section is disposed in the region that includes an edge in the lengthwise direction of the absorbing body section, then when the engagement section of the absorbing body section is engaged and fastened with the non-torso-facing surface of the support section, it can be engaged and fastened up to the edge in the lengthwise direction of the absorbing body section, making it less likely that the edge will crimp in the lengthwise direction of the absorbing body section or that the edge will catch onto the claws of the animal or onto external structures, causing the engagement between the engagement section of the absorbing body section and the non-torso-facing surface of the support section to become detached. Therefore, the absorbent article for an animal provided with such a structure allows the absorbing body section to be fitted onto the animal in a more steady manner, and as a result, leakage of excreta of the animal can be more stably and reliably prevented.

(Non-Stretchable Sheet)

Also according to the embodiment described above, as shown in FIG. 1 and FIG. 4B, the non-stretchable sheets 384 are disposed at locations corresponding in the thickness direction DT with the engagement sections 38 on the second surface $3b$ of the absorbing body section 3. When the non-stretchable sheets 384 are disposed at such locations, it is possible to form the non-stretchable portions in the engagement sections 38, and to allow the engagement sections 38, that are more susceptible to dynamic load, to be reinforced from the back surface side, so that deformation or tearing will be less likely to occur at the engagement sections. The absorbing body section 3 can therefore be more stably fitted onto the pet, and as a result, it is possible to more stably and persistently prevent leakage of excreta by the pet.

(Back Film)

Moreover, for this embodiment, as shown in FIG. 2 and FIG. 3, a back film 34 is disposed between the back sheet 32 and the absorbent body 33. The back film 34 is composed of a liquid-impermeable film that functions to keep excreta such as urine that have permeated the top sheet 31 or absorbent body 33, from leaking out through the back sheet 32 side. Incidentally, the back film 34 may be constructed of the same liquid-impermeable sheet as the back sheet 32 described above, and for example, a hydrophobic nonwoven fabric, SMS layered nonwoven fabric, liquid-impermeable plastic film, or a laminated sheet comprising any desired combination of these sheets, may be used.

Since the absorbent article for an animal of the invention comprises the specific engagement section, tail opening and elastic members as explained above, when the absorbent article for an animal has been fitted onto the body of the animal, contractive force of the elastic members acting between the dorsal region side end section and tail opening and between the abdominal region side end section and tail opening of the absorbing body section causes the engagement section of the absorbing body section to be pulled along the body surface of the animal and toward the tail opening that has a fixed location due to the tail of the animal, and force in the direction crossing with the girth direction of the animal (shearing force) acts on the section where the engagement section of the absorbing body section and the non-torso-facing surface of the support section are engaged, thus strengthening engagement between the engagement section of the absorbing body section and the non-torso-facing surface of the support section, and rendering the absorbing body section less likely to detach from the support section.

Furthermore, when the absorbent article for an animal of the invention has been fitted onto the body of an animal, the lower crotch region-facing section of the absorbing body section is pulled relatively toward both the abdominal region side end section and the tail opening by contractive force of the elastic members acting between the abdominal region side end section and tail opening of the absorbing body section, and therefore the lower crotch region-facing section more easily contacts with the lower crotch region of the animal (i.e., a gap is less likely to form between the body surface of the animal and the surface of the absorbing body section). Moreover, in the absorbing body section, since the elastic members are disposed in the regions on both outer sides in the widthwise direction of the absorbent body which are the regions corresponding to the leg-surrounding regions of the animal, those regions more easily undergo elastic deformation to follow movement of the leg-surrounding regions of the animal, and the regions can be fitted more exactly and persistently to the lower crotch region of the animal even during movement by the animal, such as walking.

This allows the absorbent article for an animal of the invention to prevent leakage of excreta, by being unlikely to detach from the body of the animal and by exactly fitting to the lower crotch region of the animal.

The present invention can be applied to a variety of absorbent articles for animals, other than a disposable diaper for a pet according to the embodiment described above, such as a (light) incontinence pad for an animal, for example. Furthermore, the absorbent article for an animal of the invention is not restricted to the embodiments described above and can incorporate appropriate combinations and modifications within a range that is not outside of the object and gist of the invention. Incidentally, the ordinal terms "first" and "second" as used throughout the present description serve merely to distinguish between the numbered embodiments and are not used to mean any relative ordering, precedence or importance.

The invention claimed is:

1. An absorbent article for an animal, the absorbent article comprising:
a support section configured to be fitted in a freely detachable manner along a region around a torso including a dorsal region and an abdominal region of an animal, and the support section having
a torso-facing surface for facing the region around the torso of the animal, and
a non-torso-facing surface located on a side opposite the torso-facing surface, and
an absorbing body section configured to be disposed along the dorsal region, a lower crotch region, and the abdominal region of the animal, and the absorbing body section having
a dorsal region side end section configured to be located on a dorsal region side of the animal, and
an abdominal region side end section configured to be located on an abdominal region side of the animal,
wherein at least one end section, among the dorsal region side end section and the abdominal region side end section, is engaged and fastened in a freely detachable manner with the non-torso-facing surface of the support section,
wherein
the absorbing body section has
a longitudinal shape with a lengthwise direction and a widthwise direction in a planar view when in an expanded state,
a first surface as a surface for facing the animal when the absorbent article is fitted onto the animal, and
a second surface as a surface on an opposite side from the first surface, and
the absorbing body section comprises, in the planar view when in the expanded state,
an engagement section disposed on the first surface of said at least one end section, among the dorsal region side end section and the abdominal region side end section located at both ends in the lengthwise direction of the absorbing body section,
an absorbent body extending in the lengthwise direction to straddle a center axis line running in the widthwise direction of the absorbing body section, and the absorbent body further extending in the widthwise direction to straddle a further center axis line running in the lengthwise direction,
a tail opening formed between the absorbent body and the dorsal region side end section, and
elastic members that impart a contractive force to the absorbing body section in the lengthwise direction, the elastic members being disposed on both outer sides in the widthwise direction of the absorbent body and having lengths in the lengthwise direction that are at least longer than a length of the absorbent body in the lengthwise direction.

2. The absorbent article for an animal according to claim 1, wherein the engagement section of the absorbing body section at least partially has a non-stretchable portion.

3. The absorbent article for an animal according to claim 1, wherein the support section is stretchable in a girth direction of the animal.

4. The absorbent article for an animal according to claim 1, wherein
the support section is constructed by a single sheet member that has a first direction corresponding to a girth direction of the animal and a second direction that is orthogonal to the first direction,
the single sheet member includes
the torso-facing surface facing the region around the torso of the animal, and
the non-torso-facing surface located on the side opposite the torso-facing surface, and
the sheet member has a support section engagement section configured to engage with the non-torso-facing surface of the support section, on the torso-facing surface of one end section among both end sections in the first direction.

5. The absorbent article for an animal according to claim 1, wherein
the absorbing body section has a thickness direction that is orthogonal to both the lengthwise direction and the widthwise direction, the absorbing body section comprises a laminated body that includes, in the thickness direction,
at least a liquid-permeable top sheet located on a first surface side,
a liquid-impermeable back sheet located on a second surface side, the absorbent body disposed between both of these sheets, and
a pair of side sheets located on the first surface side of the top sheet,
wherein the laminated body has a border section with a different number of layers in the widthwise direction, in the planar view with the absorbing body section in the expanded state, and
the engagement section of the absorbing body section extends in the widthwise direction to straddle at least the border section.

6. The absorbent article for an animal according to claim 1, wherein the engagement section of the absorbing body section is disposed in a region that includes an edge in the lengthwise direction of the absorbing body section, on the first surface on said at least one end section among the dorsal region side end section and abdominal region side end section of the absorbing body section.

7. The absorbent article for an animal according to claim 1, wherein
the engagement section of the absorbing body section has
a plurality of engaging protrusions that protrude from the first surface, each of the plurality of engaging protrusions having
a shaft portion running from the first surface of the absorbing body section, and
at a tip of the shaft portion, a wide portion running in a direction in which an outer peripheral surface of the shaft portion widens.

* * * * *